United States Patent

Takahashi

[11] 4,086,583
[45] Apr. 25, 1978

[54] LIGHT SOURCE AND EXPOSURE CONTROL DEVICE FOR ENDOSCOPIC PHOTOGRAPHY

[76] Inventor: Nagashige Takahashi, No. 4-1, Nishi-machi, Kokubunji-shi, Tokyo, Japan

[21] Appl. No.: 780,158

[22] Filed: Mar. 22, 1977

[30] Foreign Application Priority Data

Mar. 24, 1976 Japan .............................. 51-35604[U]

[51] Int. Cl.² .......................... G03B 29/00; A61B 1/06
[52] U.S. Cl. ............................................ 354/62; 128/6
[58] Field of Search ................... 354/32, 33, 34, 60 F, 354/62, 63, 126; 128/4, 6

[56] References Cited

U.S. PATENT DOCUMENTS 3,599,630  8/1971  Sato et al. .............................. 354/62

Primary Examiner—L. T. Hix
Assistant Examiner—M. L. Gellner
Attorney, Agent, or Firm—Sughrue, Rothwell, Mion, Zinn and Macpeak

[57] ABSTRACT

An endoscopic photography system including a side shutter 4 for a light source 3, a camera 5 including means for closing the side shutter 4 before the camera shutter is opened, an MSMV 12 for delaying the side shutter opening and the cumulative object light integration until the light source has reached a maximum intensity, and a level detector 8 for closing the side shutter to terminate the photographic exposure when the integrated light quantity signal reaches a predetermined value.

6 Claims, 2 Drawing Figures

LIGHT SOURCE AND EXPOSURE CONTROL DEVICE FOR ENDOSCOPIC PHOTOGRAPHY

BACKGROUND OF THE INVENTION

This invention relates an automatic exposure control and light source control device for an endoscope photographic system for taking internal pictures of living body tissue.

Although lighting the object is essential for internal body photography with an endoscope, the operating conditions of the light for this purpose are limited. More specifically, a relatively high speed shutter control is required for obtaining an image which is both clear and sharp, and for this purpose it is essential to brightly illuminate the object. However, as a strong light source has a damaging thermal influence on body tissue, a photographic synchronization type lighting system in which the light source is only exposed for the short period of time necessary for the photographing has been employed in this art. In the conventional synchronization type lighting system, a light source side shutter is provided in addition to the camera shutter. The object illumination is effected only when the film is exposed, or from immediately before to just after the film exposure, by a device which, with the camera shutter opened, opens and closes the light source side shutter, or controls either the exposure start or finish operation by means of the camera shutter or the light source side shutter, thereby shortening the period of tissue illumination and thermal exposure.

In photographic systems of this type, an automatic exposure control device is typically combined with the above-described light source control device to simplify the photographic operation. The automatic exposure control device is so desinged that part of the light reflected from the object is received by a photosensitive element whose output current is integrated, and when the integration value reaches a certain level a film exposure completion signal is produced. With an automatic exposure control device and a light source control device used in combination, high intensity light is applied to the body tissue or object such that the film exposure can be effected with the camera shutter opened (that is, the integration operation is commenced simultaneously with the opening of the camera shutter), whereby the synchronization of the object lighting timing with the photographic timing, and the coincidence of the former with the start of the light quantity integration, can be obtained.

In such a conventional device, the light quantity integration preparation is completed or the input gate of the integrator is closed before the film exposure is commenced. Therefore, during the period of time from the preparation completion to when the object lighting is fully implemented, noise signals and drifts may occur in the automatic exposure control circuit, and this electrical instability results in exposure control errors.

SUMMARY OF THE INVENTION

According to this invention, the automatic film exposure control device minimizes errors due to electrical instability, to thereby implement a highly accurate photographic operation.

Briefly, and in accordance with the present invention, an endoscopic photography system includes a side shutter for a light source, a camera including means for closing the side shutter before the camera shutter is opened, an MSMV for delaying the side shutter opening and the cumulative object light integration until the light source has reached a maximum intensity, and a level detector for closing the side shutter to terminate the photographic exposure when the integrated light quantity signal reaches a predetermined value.

In this manner the full intensity energization of the light source is fully synchronized with the integration of the reflected light, thereby minimizing both noise and drift errors as well as the thermal effects of the light source. The latter is also energized through a gated semiconductor such as an SCR or a TRIAC, whereby low level tissue illumination is easily implemented for diagnostic observation.

DETAILED DESCRIPTION OF THE PREFERRED EMBODIMENT

Figure 1:
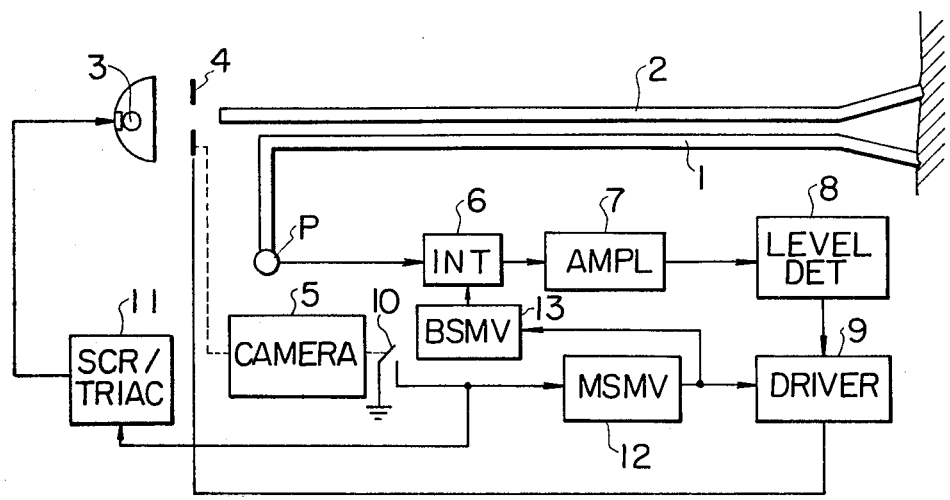
FIG. 1 shows a block diagram of an endoscope light source control device according to this invention.

Referring to FIG. 1, a body tissue lighting fiber optic system 2 is cooperatively disposed with respect to an image transmitting fiber optic system 1 for observation and photography by an endoscope. A light source 3 is positioned at the inlet of the fiber optic system 2 through the intermediary of a controllable side shutter 4.

A camera 5 is disposed at the light outlet of the fiber optic system 1, and a photo-sensitive element P is also disposed at such outlet to receive part of the photographic light directed toward the camera 5. The output current from the photo-sensitive element P is applied to an integrator 6, whose output in turn is amplified by an amplifier 7. The amplified integration value thus obtained is applied to a detector 8. A signal is produced by the detector 8 when the integration value reaches a predetermined level (which is necessary for a suitable exposure), and this signal is applied to a shutter driving circuit 9 whose output then closes the light source side shutter 4.

Reference numeral 10 designates a switch which cooperates with the shutter release operation of the camera 5, and which is closed just before the shutter is opened. The switch 10 may be operated by one of the double shutter release wires, or by the FP contact of the camera 5. The (ground) signal produced with the switch 10 is closed is applied, as a power increasing control signal, to a circuit 11 comprising a phase angle conduction control element, such as an SCR or a TRIAC, to thereby control the energization of the light source 3. The switch signal is also applied, through a monostable multivibrator delay circuit 12 and a flip-flop circuit 13, to the integrator 6, and to the shutter driving circuit 9 whose output opens the light source side shutter 4. In addition, a mechanical coupling mechanism (not shown) is provided which, in the preliminary camera release operation, closes the side shutter 4 when the switch 10 is closed or just before it is closed.

To observe the body object with the naked eye or through the camera viewfinder, an electric power of less than the full rating is applied to the light source 3, and under these conditions the object is illuminated with the side shutter opened. Since this lighting condition is obtained by using a reduced power level, no adverse or damaging thermal effects result with respect to the adjacent body tissue.

Figure 2:
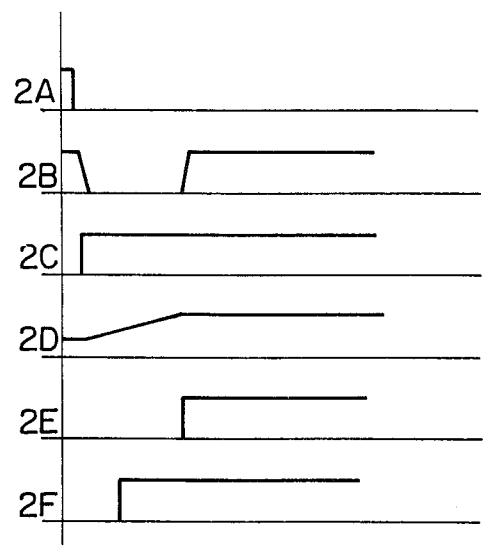
FIGS. 2A – 2F show waveform and timing diagrams of various signals appearing in the circuit of FIG. 1.

In a photographic operation, the side shutter 4 is closed (FIG. 2B) in cooperation with the camera release (FIG. 2A), and simultaneously the switch 10 is closed. As a result, the circuit 11 applies an increased voltage to the light source 3 (FIG. 2C), and the intensity of the source 3 increases during a rise time (FIG. 2D) until it reaches a stabilized, full rated level. This rise time is substantially constant as seen in FIG. 2D, and the camera shutter is opened during such rise time, as shown in FIG. 2F. After the delay provided by the circuit 12, which corresponds to the light intensity rise time, an opening signal for the side shutter 4 is applied to the shutter driving circuit 9, and an integration start signal is applied through the flip-flop circuit 13 to the integrator 6, as shown by the waveform of FIG. 2E. By such time the light source 3 has reached a stabilized intensity level.

Part of the light from the object is detected by the photo-sensitive element P, and the quantity of such light is accumulated by the integrator 6. When the integrated light quantity reaches a predetermined value, a closing signal is delivered to the shutter driving circuit 9 by the level detector 8. As a result, the side shutter 4 is closed, thus completing the film exposure.

Thus, according to this invention, before the camera shutter is opened to photograph the endoscopic object, the lighting of the object is suspended by closing the side shutter, and full electrical power is temporarily applied to the light source in synchronization with the shutter release operation. The side shutter is subsequently opened when the light intensity reaches a stable, maximum value, and the input gate of the integrator is simultaneously closed, thus commencing the cumulative light quantity measurement. Thus, the film exposure start time (the time at which the full object lighting is commenced by opening the side shutter) and the integration start time (the light quantity measurement start time) are fully synchronized. Accordingly, noise and drift errors due to the integration being started before the actual film exposure are minimized. Furthermore, since the film exposure is carried out with a maximum light intensity, a high speed shutter operation is realized. In addition, since the side shutter is closed before the camera shutter is opened, synchronized photography in which the light source response delay is eliminated can be easily achieved.

Light intensity control is implemented by controlling the power applied to the lamp, whereby such intensity is held at a comfortable level well below the maximum rating of the lamp for ordinary diagnostic observations. Thus, the provision of a conventional mechanical diaphragm for controlling the quantity of light is unnecessary.

What is claimed is:

1. In an endoscopic photography system including a light source, an endoscope, a side shutter disposed between the light source and a light inlet of said endoscope, a camera disposed adjacent a light outlet of said endoscope, a photosensitive element disposed adjacent said light outlet, circuit means for integrating the output of the photo-sensitive element, and circuit means for detecting when the integration value reaches a predetermined level, an improved side shutter and automatic exposure control system characterized by:
    (a) means for closing the side shutter and increasing the intensity of the light source in synchronization with the camera release and before the camera shutter is opened, and
    (b) delay means responsive to the camera release for opening the side shutter and enabling the integrating circuit means when the light source intensity has reached a stable, maximum value.

2. An endoscopic photography system as defined in claim 1, wherein the means for increasing the intensity of the light source comprises a gate controlled semiconductive element.

3. An endoscopic photography system as defined in claim 2, wherein the delay means comprises a monostable multivibrator.

4. An endoscopic photography system as defined in claim 3, wherein the time delay provided by the delay means corresponds to the time required for the intensity of the light source to reach a stable, maximum value after its energization is increased.

5. An endoscopic photography system as defined in claim 1, wherein the delay means comprises a monostable multivibrator.

6. An endoscopic photography system as defined in claim 1, wherein the time delay provided by the delay means corresponds to the time required for the intensity of the light source to reach a stable, maximum value after its energization is increased.

* * * * *